US010352919B2

(12) United States Patent
Kaipainen et al.

(10) Patent No.: US 10,352,919 B2
(45) Date of Patent: Jul. 16, 2019

(54) SOLIDS LEVEL INDICATOR

(71) Applicant: Andritz Inc., Glens Falls, NY (US)

(72) Inventors: Vesa Kaipainen, Kotka (FI); Scott Arthur Pope, Atlanta, GA (US); Keith Vogel, Queensbury, NY (US)

(73) Assignee: Andritz Inc., Glens Falls, NY (US)

( * ) Notice: Subject to any disclaimer, the term of this patent is extended or adjusted under 35 U.S.C. 154(b) by 450 days.

(21) Appl. No.: 15/058,734

(22) Filed: Mar. 2, 2016

(65) Prior Publication Data

US 2016/0258924 A1 Sep. 8, 2016

Related U.S. Application Data

(60) Provisional application No. 62/128,580, filed on Mar. 5, 2015.

(51) Int. Cl.
| | | |
|---|---|---|
| *G01N 33/46* | (2006.01) | |
| *G01F 23/20* | (2006.01) | |
| *G01F 23/00* | (2006.01) | |
| *G01F 23/22* | (2006.01) | |

(52) U.S. Cl.
CPC .............. *G01N 33/46* (2013.01); *G01F 23/20* (2013.01); *G01F 23/003* (2013.01); *G01F 23/226* (2013.01)

(58) Field of Classification Search
CPC ................................. G01N 33/46; G01F 23/20
See application file for complete search history.

(56) References Cited

U.S. PATENT DOCUMENTS

| | | | | |
|---|---|---|---|---|
| 2,376,473 A | 5/1945 | Brockett | | |
| 2,680,298 A | 6/1954 | Obenshain | | |
| 2,698,362 A * | 12/1954 | Bozich | ................. | G01F 23/226 200/61.21 |
| 3,971,254 A * | 7/1976 | Sherman | ................. | G01F 23/00 73/290 R |
| 4,964,301 A | 10/1990 | Lysen | | |
| 9,383,243 B1 * | 7/2016 | Schaefer | ............... | G01F 23/003 |
| 2013/0081480 A1 | 4/2013 | Giovanoni et al. | | |
| 2015/0330555 A1 * | 11/2015 | Vogel | ..................... | F16M 1/00 406/63 |

FOREIGN PATENT DOCUMENTS

| | | |
|---|---|---|
| EP | 0395629 | 10/1990 |
| EP | 1237724 | 9/2002 |

OTHER PUBLICATIONS

Nierhaus, Thomas, Extended European Search Report, dated Jul. 29, 2016, European Patent Office.
Eduardo Pino Medel, First Office Action, Chilean Patent Application No. 513-2016, pp. 1-6, dated Jan. 23, 2018, Chile.

* cited by examiner

*Primary Examiner* — Jamel E Williams
(74) *Attorney, Agent, or Firm* — Robert Joseph Hornung

(57) ABSTRACT

This disclosure describes a level indicator assembly for measuring the level of solids in a vessel. The level indicator may desirably comprise a solid shaft extending into a vessel. The shaft may have paddle connected to an interior end of the shaft and an external sensor attached to an exterior end of the shaft. A support structure may engage the sensor to prevent at least a portion of the sensor from moving. By keeping a portion of the sensor stationary, the sensor may measure the change in torsional force exerted on the shaft. By locating the sensor external to the vessel, operators may remove and replace sensors without accessing either the vessel interior or the portions of the level indicator assembly that extend into the vessel.

24 Claims, 8 Drawing Sheets

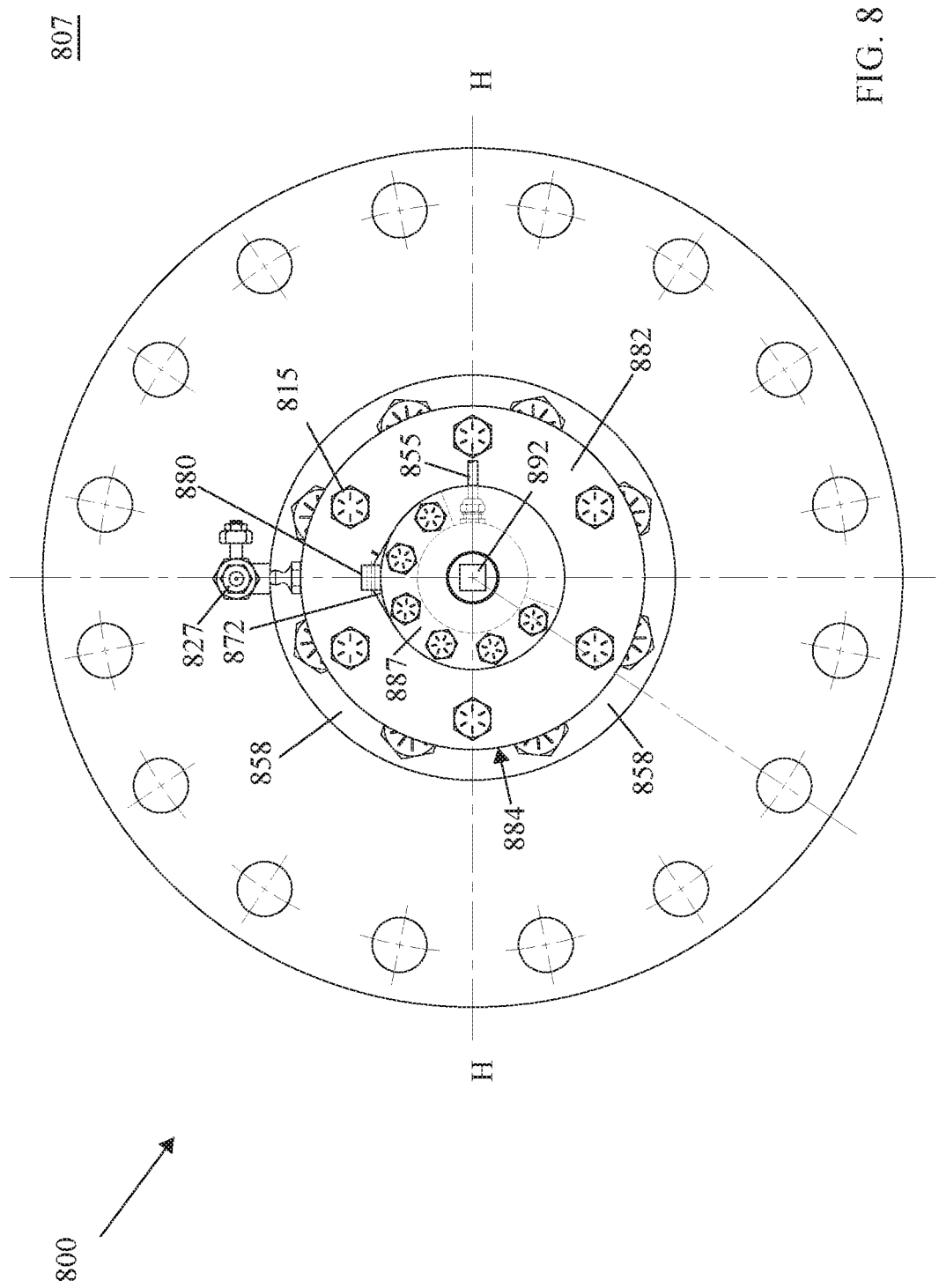

SOLIDS LEVEL INDICATOR

RELATED APPLICATION

This application claims the benefit of U.S. provisional patent application 62/128,580, filed on Mar. 5, 2015, the entirety of which is incorporated herein by reference.

BACKGROUND OF THE INVENTION

1. Technical Field

The present disclosure relates generally to an assembly for determining the level of solid particles in a vessel, including storage vessels such as chip bins and silos, as well as processing vessels such as chemical digesters and impregnation vessels. The present disclosure relates more particularly to a method and system for detecting the level of wood chips or other biomass used in the manufacture of paper pulp or other products from lignocellulosic biomass.

2. Related Art

The present disclosure describes a solids level indicator. Although the solids level indicator may be used in processes or industries involving the movement of solids or fluids or both solids and fluids through a vessel, subsequent exemplary may refer to chip bins, impregnation vessels, and continuous digesters used in the pulp and paper industry.

Mill operators use mechanical solids level indicators in holding vessels such as silos, storage bins, pipes, and treatment vessels such as chemical digesters and impregnation vessels to estimate the height of the pile of solids within the vessel. For example, in the pulp and paper industry, mill operators may use one or more continuous chemical digesters to produce pulp. Continuous digesters tend to be large, vertically oriented reactor vessels that tower over a pulp mill. These digesters use caustic liquors to break down pretreated lignocellulosic material into paper pulp and byproducts. Although methods vary, operators generally feed solids such as softened wood chips or other lignocellulosic material into the top of a continuous digester. Generally, the continuous digester is either a vapor phase continuous digester or a hydraulic phase continuous digester.

Inside a vapor phase continuous digester, the chips collect in a conical pile. The conical pile gradually sinks under its own weight into a mire of caustic liquor and proto-pulp. The caustic liquor denatures lignin, a protein in the wood chips that naturally holds the cellulosic fibers together. As the protein itself dissolves into the liquor, the wood chip's cellulosic fibers disintegrate into viscous proto-pulp. The liquor and proto-pulp ooze slowly down the length of the vertical vessel until the liquor and proto-pulp reach an outlet port at the bottom of the continuous digester. At the bottom, operators pump the proto-pulp to downstream equipment for further processing and cleaning. In hydraulic phase continuous digesters, the liquor level generally exceeds the chip level. Mechanical solids indicators allow operators to calculate the top level of the chips and thereby monitor pulp production and control the rate at which new chips enter the vessel.

Typical mechanical level indicators generally have a shaft disposed in a shaft housing that extends through a pipe in the vessel wall. The shaft housing has an exterior end bolted to the vessel wall. In this manner, the shaft housing generally resists torsional movement. The shaft may be hollow and is disposed within the shaft housing. The hollow portion of the shaft may house a sensor as shown in U.S. Pat. No. 3,971,254, the entirety of which is incorporated herein by reference. The sensor is typically a strain gauge. The shaft housing's interior end typically has a paddle extending generally perpendicularly to the length of the shaft housing and the paddle is typically oriented transversely to the direction that the solids flow. That is, a single paddle generally extends from the side of the shaft housing and crosses the path of the usually downward-moving solids. As the solids move through a vessel, the solids exert a force on the paddle. The paddle, being connected to the side of the shaft housing, transforms the downward force of the solid particles into a torsional force. The shaft within the shaft housing, being in torsional communication with the paddle, communicates the torsional force to a strain gauge or other sensors, located within the shaft.

Although the shaft may or may not rotate visibly, the sensors measure the torsional force (e.g. the twisting force) and shear stress on the shaft. The degree to which the solids particles impart torsional force and create shear stress on the shaft housing and shaft can be used to ascertain the mass of solids above the paddle. The mass, together with the known density of the solids can be used to calculate the position of the top level of the solids pile. Furthermore, in holding vessels and treatment vessels, solid level indicators may be disposed at several elevations along the height of the vessel.

Solids level indicators may also have shear pins, which extend through the shaft housing into the shaft. These shear pins generally prevent the shaft from rotating within the shaft housing. Shear pins generally withstand less torsional force than the paddle or shaft itself. If the torsional stress on the paddle and shaft becomes excessive, the shear pins typically break before the paddle or shaft breaks. When a shear pin breaks, the paddle rotates downwardly to a neutral vertical position. That is, the paddle no longer crosses the path of the solid particles. While this protects the paddle, a paddle in the neutral position can no longer detect the downward force of the chips and therefore can no longer measure the chip level. While generally successful, this design has several drawbacks.

If the solids level indicator is used in a digester, impregnation vessel, or other treatment vessel that operates under high temperature and pressure, the high temperature may damage the electronic sensors within the hollow shaft and the temperature may cause the solids level indicator to expand unevenly. Uneven expansion can disrupt readings. Additionally, manufacturers generally laminate multiple sensors inside of the hollow portion of the shaft. If the mass of solids is sufficiently large, the solid particles may bend and distort the hollow shaft and shaft housing. Small distortions in the shaft straightness may dislodge or damage the sensors, thereby rendering the solids level indicator nonfunctional. Shaft distortion may further distort the paddle. Laminating these sensors or servicing these sensors requires precision and the efforts of a skilled worker in a temperature-controlled environment.

Extracting a solids level indicator from an active treatment vessel would expose an operator to fluctuating, unsafe process conditions. For these reasons, these sensors generally cannot be installed at the mill site on an active treatment vessel such as a continuous digester or impregnation vessel. As a result, the mill operator generally shuts down the mill before extracting and replacing damaged solids level indicators. If the mill operator does not have spare solids level indicators available, the operator ships the broken solids level indicators to the manufacturer to be rebuilt. Replacing the sensors, and pretreating the solids level indicators to protect the solid level indicators from process conditions (such as caustic liquor, high temperatures and corrosive steam) can add weeks to a mill shutdown, which results in loss of production and reduced work hours for mill employees.

To avoid some of these problems, manufactures developed solids level indicators with magnetic sensors fixed to the exterior ends of the shaft housing and shaft such as the one depicted in U.S. Pat. No. 4,964,301, the entirety of which is incorporated herein by reference. However, to obtain accurate readings, the entire solids level indicator had to be precisely designed to the operating conditions of a particular continuous digester. For example, the length and thickness of the shaft housing and shaft would vary depending upon whether the digester was a vapor phase digester or a hydraulic phase digester. Additionally, the paddle area would vary depending not only upon the type of digester but also upon the location of the solids level indicator within the digester. For example, if one imagines a vapor phase digester and a hydraulic phase digester having substantially the same operating capacity, then the area of hydraulic phase digester paddles are generally greater than the area of vapor phase digesters paddles. The chips in a hydraulic phase digester are suspended in liquid and therefore generally exert less force on the paddles; the paddles generally have a larger surface area to compensate. However, mill operators tend to use hydraulic phase digester plates in the middle and bottom process zones of vapor phase digesters because they notice that the liquor level can rise into these process zones. Unfortunately, the liquor level in vapor phase digesters can fluctuate and return below the solids level indicator in the middle and bottom process zones. When the liquor falls below these solids level indicators, the liquor no longer offsets the weight of the chips, and the chips can bear down on the large-area paddles with excess force. The excess weight can surpass the loads for which the paddles were designed, which breaks the shear pins. As a result, the paddle on the solids level indicator rotates 90 degrees to a position in which the paddle no longer crosses the path of the solids. In this manner, the solids level indicator may be saved but rendered non-functional.

Inactive solids level indicators reduce the accuracy of top level measurements. To the extent operators extrapolate other process conditions from the top level data, top level inaccuracies can reduce the accuracy of other process measurements. This may in turn increase the risk that improper processes regulation will create safety hazards, or loss of production due to premature maintenance shutdown.

Accordingly, there is a long felt need to have a solids level indicator that can provide accurate level measurements within a vessel while overcoming the limitations of the prior art.

SUMMARY OF THE INVENTION

The problem of loss of production due to rebuilding the hollow shaft and sensors of conventional solids level indicators is mitigated by using a one or more solids level indicators having an modular external sensor attached to the exterior end of a solid torsion shaft, wherein the modular external sensor has a rotary end torsionally communicating with the shaft exterior end and a stationary end connected to a stationary support structure, and wherein the modular external sensor is configured to be removed, such that removal and replacement of the modular external sensor does not require removing the solid torsion shaft from the vessel.

An exemplary solids level indicator may withstand downward force in a range of between about 500 Newton-meters (Nm) to about 7500 Nm. Previously, operators used different paddle sizes for different solids level indicators disposed in the vessel or changed the size of the paddles depending on the load the paddle was expected to experience. This required removing the torsion shaft from the vessel to access the paddle at the shaft interior end. Applicant has recognized that the force an exemplary solids level indicator is able to withstand is dependent on the density of the chips and whether the biomass in the vessel is under liquor level or over liquor level.

To mitigate the problem of paddle failure due to inconsistent solids load, including inconsistent solids load resulting from different paddle sizes and inconsistent liquor level in chemical digesters, Applicant discloses a solids level indicator comprising a torsion spring in torsional communication with the solid torsion shaft, wherein the torsion spring has a first spring end in torsional communication with the torsion shaft and a second spring end distally disposed from the first spring end, whereby the second spring end fixedly engages a support structure or a shaft housing, such that the torsion spring stores excess torsional force from the torsion shaft. The torsion spring may be further configured to provide a torsional force to the torsion shaft in a direction opposite the direction of the torsional force exerted on the paddle by the mass of solids, thereby automatically returning the paddle to measurement-ready position. In this manner, the torsion spring may ensure that the amount of paddle surface area exposed to the mass of solids is proportional to the amount of downward force the solids exert on the paddle. In accordance with this disclosure, an exemplary solids level indicator with a torsion spring may allow operators to use one paddle size for each solids level indicator extending to a vessel, regardless of where the solids level indicators are located along the height of the vessel. In this manner, the exemplary embodiments reduce the need for operators to withdraw the torsion shaft to access the paddle.

It is a further object of the present disclosure to allow operators to access easily the torsion spring while the vessel is operational to allow mill operators to replace or re-calibrate the torsion spring as needed.

It is a further object of the present disclosure to allow operators to adjust the angle at which the paddle of the solids level indicator crosses the path of moving solids while the vessel, particularly a chemical digester, is operational and thereby allow operators to prolong the useful life of solids level indicators by responding to fluctuating operating conditions.

It is a further object of the present disclosure to calibrate multiple exemplary solid level indicator assemblies disposed at varying vertical heights in a vessel to accommodate the operating conditions of a particular vessel.

In an exemplary embodiment, the solids level indicator may further comprise a plug cap with multiple bore holes arranged at intervals around the plug cap. The plug cap torsionally communicates with the torsion shaft and a shear pin extends through a support structure into the plug cap to orient the plug cap. The plug cap's orientation corresponds to a paddle deflection angle measured from a horizontal line bisecting the torsion shaft. Operators may remove the shear pin, rotate the plug cap to a subsequent bore hole to change the paddle's deflection angle before returning the shear pin to the support structure and subsequent bore hole to secure the plug cap at a new orientation, thereby changing the paddle's deflection angle. The plug cap with multiple bore holes may allow operators to use a singled-sized paddle at different elevations along the height of the vessel.

It is an object of the present disclosure to use a stronger solid torsion shaft that would not have the same fail points as prior hollow shafts, the prior hollow shafts having internal sensors and more complex construction. As a result, an exemplary sensor may be less susceptible to heat and internal vessel conditions. An exemplary modular external sensor may be smaller, than conventional designs such that the exemplary modular external sensor can be lightweight and may be stored using less space than prior sensors. In other exemplary embodiments, a hollow torsion shaft may be used in lieu of a solid torsion shaft.

It is also an object of the present disclosure to be able to use existing shaft housings on vessels and configuring the exterior end of the shaft to accept an external sensor. The shaft may be machined, printed, forged, pressed, or manufactured by other means commonly used in the industry. An exemplary solids level indicator may be made of suitable materials including type 316L and 1.4462 (stainless duplex steel).

In an exemplary embodiment, the stationary support structure may include mounting arms mounted to the vessel and configured to hold the stationary end of the modular external sensor in place. The modular external sensor may be configured to measure deflection between the rotary end of the external sensor and the stationary end of the external sensor. An exemplary embodiment may further comprise shear pins extending through the support structure and into a plug cap or the shaft housing.

In other exemplary embodiments, the shear pins may be replaced by a torsion spring that releases if the torsional force exceeds a predetermined threshold. Using a torsion spring-loaded construction may allow operators to use a singled-sized paddle at different elevations along the vessel. The torsion measurement is generally logarithmic, therefore; using a uniform paddle size may permit a significantly wider measurement area over existing designs. Another exemplary solids level indicator may use angle measurement instead of a torsion measurement. Yet other exemplary solids level indicators may use a combination of angle and torsion measurement. In still other exemplary embodiments, the modular external sensor may be a piezoelectric sensor.

The solids level indicator may be used in vessels that contain solid particles or solids suspended in or otherwise present with liquid. In certain exemplary embodiments, the solids level indicator may be used in chip bins, continuous digesters, impregnation vessels, silos, pipes, and other holding or treatment vessels for solid particles, including lignocellulosic material. Solids level indicators may be disposed at multiple elevations and locations within the vessel.

BRIEF DESCRIPTION OF THE DRAWINGS

The foregoing will be apparent from the following more particular description of exemplary embodiments of the disclosure, as illustrated in the accompanying drawings in which like reference characters refer to the same parts throughout the different views. The drawings are not necessarily to scale, with emphasis instead being placed upon illustrating the disclosed embodiments.

FIG. 8 is a front view of an exemplary solids level indicator assembly having a support sleeve and a multi-bore plug cap.

DETAILED DESCRIPTION OF THE INVENTION

Figure 1:
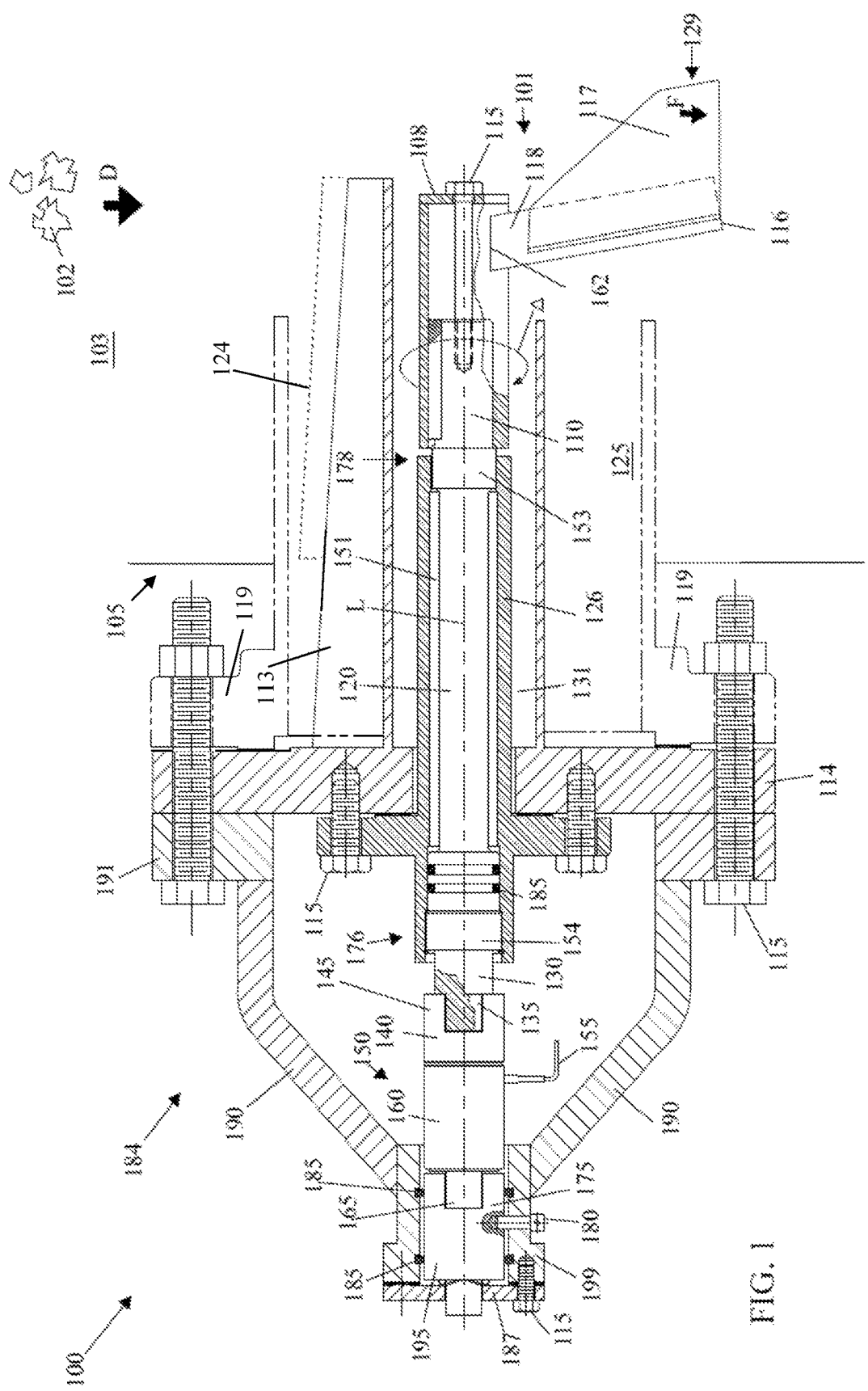
FIG. 1 depicts a cross-sectional view of an exemplary solids level indicator assembly having a detachable modular external sensor with a rotary end attached to the exterior end of the solid torsion shaft and a stationary end torsionally engaged to a cap plug secured by mounting arms of a support structure.

The following detailed description of the preferred embodiments is presented only for illustrative and descriptive purposes and is not intended to be exhaustive or to limit the scope and spirit of the invention. The embodiments were selected and described to best explain the principles of the invention and its practical application. One of ordinary skill in the art will recognize that many variations can be made to the invention disclosed in this specification without departing from the scope and spirit of the invention.

Corresponding reference characters indicate corresponding parts throughout the several views. Although the drawings represent embodiments of various features and components according to the present disclosure, the drawings are not necessarily to scale and certain features may be exaggerated in order to better illustrate embodiments of the present disclosure, and such exemplifications are not to be construed as limiting the scope of the present disclosure in any manner.

References in the specification to "one embodiment", "an embodiment", "an exemplary embodiment", etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described.

FIG. 1 is a side cross-sectional view of an exemplary solids level indicator assembly 100. FIG. 1 depicts a vessel 105 having a wall 107. A mounting flange 119 extends through the wall 107 to define a conduit 125. The conduit 125 may be configured to accommodate different measuring equipment, and therefore the conduit 125 may be too wide to receive an exemplary solids level indicator 101 without aid. As a result, an indicator adapter 113 may extend through the conduit 125. The indicator adapter 113 may have an indicator adapter flange 114 disposed on the mounting flange 119. One or more fasteners 115 or other suitable fastening means engage the indicator adapter flange 114 to the mounting flange 119. The indicator adapter 113 defines an adapter conduit 131, which may extend into the vessel interior 103. The indicator adapter 113 may further comprise a protective sleeve 124 that extends over a paddle cap 108 on the solids level indicator 101.

The shaft housing 126 is disposed within the adapter conduit 131. Fasteners 115 or other suitable fastening means rigidly engage the shaft housing 126 to the indicator adapter flange 114. In this manner, the shaft housing 126 resists a twisting movement resulting from torsional force Δ communicated through the torsion shaft 120. The shaft housing 126 has a housing interior end 178 and a housing exterior end 176. The housing exterior end 176 is disposed outside the vessel 105. A torsion shaft 120 is disposed within the shaft housing 126. The torsion shaft 120 has a shaft exterior end 130 and a shaft interior end 110. The shaft interior seal 153 provides sealing engagement between the shaft housing interior end 178 and the torsion shaft 120. A bushing or other bearing (not depicted) may be disposed between the shaft interior seal 153 and the housing interior end 178. The shaft interior seal 153 may further comprise sealing mechanisms 185, which may comprise O-rings, mechanical seals, or other suitable seal configured to isolate one side of a component from the other side. Similarly, the torsion shaft 120 has a shaft exterior seal 154 at the housing exterior end 176. The shaft exterior seal 154 may likewise further comprise sealing mechanisms 185. The shaft exterior seal 154 provides sealing engagement between the shaft housing exterior end 176 and the torsion shaft 120. The area between the shaft exterior seal 154, the shaft interior seal 153, the body of the torsion shaft 120 and the inner wall of the shaft housing 126 defines a grease channel 151, which may be filled with grease or other lubricant to insulate the torsion shaft 120 from the process conditions in the vessel interior 103. The grease may further facilitate twisting movement of the torsion shaft 120 within the shaft housing 126.

The shaft interior end 110 extends past the shaft interior seal 153 and the housing interior end 178 into a paddle cap 108. The paddle assembly 129 torsionally communicates with the torsion shaft 120 through the paddle cap 108. The paddle cap assembly 129 comprises a paddle 117 engaged to a paddle arm 118 having a first end 162 opposite a second end 116. The first end 162 of the paddle arm 118 engages the paddle cap 108. In certain exemplary embodiments, the first end 162 of the paddle arm 118 extends through the paddle cap 108 into the shaft interior end 110. In this manner, the paddle assembly 129 is in torsional communication with the torsion shaft 120. In other exemplary embodiments, the first end 162 of the paddle arm 118 does not extend into the torsion shaft 120. A fastener 115 or other engaging means engages the paddle cap 108 to the shaft interior end 110 and thereby renders the paddle assembly 129 in torsional communication (e.g. able to convert or transmit the force F of the solids to torsional force Δ) with the torsion shaft 120. It will be understood that a combination of the above described paddle assembly 129 to torsion shaft 120 engagement methods or other paddle assembly 129 to torsion shaft 120 engagement methods configured to transfer the force F the solids 102 exert on the paddle 117 to the torsion shaft 120 are within the scope of this disclosure.

The paddle 117 extends substantially perpendicularly from the length L of the torsion shaft 120, such that the paddle 117 is transversely oriented to the direction of solid particle flow D. As the solids 102 move downwardly through the vessel interior 103, the solids 102 exert a force F on the paddle 117. The paddle 117 converts this downward force F into a torsional force Δ, which the solid torsion shaft transfers along the length L of the torsion shaft 120 into the modular external sensor 150.

The modular external sensor 150 comprises a stationary end 160 adjacently disposed to a rotary end 140. The modular external sensor 150 may further comprise a wire 155 configured to transmit an electrical signal from the modular external sensor 150 to signal processing equipment (not depicted). The wire 155 may extend from the stationary end 160 through a hole in the support structure 184. In other exemplary embodiments, the electrical signal may be wirelessly transmitted. By measuring the distortion in electric fields, operators may accurately determine where the level of solid particles resides at a given measurement.

The rotary end 140 is adjacently disposed to the shaft exterior end 130. In the embodiment depicted in FIG. 1, the shaft exterior end 130 has a male adapter 135 extending into a female adapter 145 in the rotary end 140 of the modular external sensor 150 and is thereby in torsional communication with the adjacently disposed rotary end 140 when the modular external sensor 150 is adjacently disposed to the shaft exterior end 130. That is, the rotary end 140 receives the torsional force Δ from the torsion shaft 120 through the shaft exterior end 130. It will be understood that other structures configured receive torsional force Δ from the torsion shaft or otherwise place an adjacently disposed modular external sensor 150 in torsional communication with the shaft exterior end 130 are considered to be within the scope of this disclosure. By way of example, these other structures may include a female adapter in the shaft exterior end 130 and a male adapter on the rotary end 140 of the modular external sensor 150. Certain exemplary embodiments may have more than one modular external sensor 150 adjacently disposed to one another such that adjacent sensors are in torsional communication. Other structures configured to place an adjacently disposed modular external sensor 150 in torsional communication with the torsion shaft 120 may include, screws, bolts, pins, clamps, a combination of male and female adapters, receivers, adapters disposed between the modular external sensor 150 and the torsion shaft 120, magnets, or a combination thereof. In certain exemplary embodiments, the external modular sensors 150 may be a strain gauge, an angle gauge, a torque transducer, a piezoelectric sensor, or a combination thereof. In still other exemplary embodiments, an external modular sensor 150 may contain more than one sensor.

A support structure 184 comprising mounting arms 190 engage the stationary end 160 of the external sensor 150 directly. In other exemplary embodiments, the mounting arms 190 may engage the stationary end 160 of the external sensor 150 indirectly through a plug cap 195. In still other exemplary embodiments, the mounting arms 190 may engage the stationary end 160 of the external sensor 150 indirectly through a sleeve or other material disposed between the stationary end 160 of the external sensor 150 and the mounting arms 190.

The mounting arms 190 may have a flange end 191 that engages the indicator adapter flange 114. Fasteners 115 secure the flange end 191 of the mounting arms 190 to indicator adapter 113. In other exemplary embodiments, the indicator adapter 113 may be absent and fasteners 115 may secure the flange end 191 of the mounting arms 190 to the flange 119 that defines conduit 125. In other exemplary embodiments, it may be desirable to secure the flange end 191 of the mounting arm 190 to a plate engaging the vessel 105. The support structure 184 helps ensure the solids level indicator assembly 100 is grounded in the vessel 105 so as to accommodate vibrations emanating from an active vessel 105, while further preventing the stationary end 160 of the modular external sensor 150 from rotating. In certain exemplary embodiments, the indicator adapter flange 114 may be disposed between the flange 119 that defines the conduit 125 and the flange end 191 of the mounting arms 190.

Figure 2:
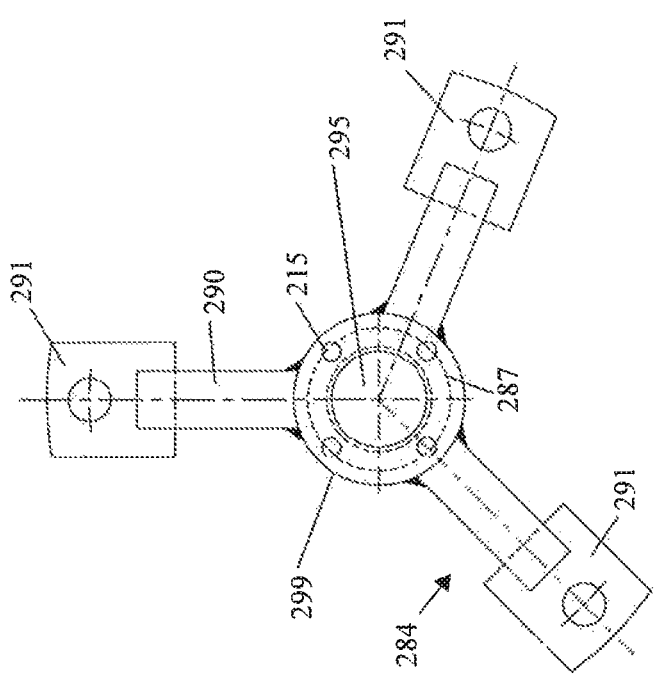
FIG. 2 is front view facing the vessel of the exemplary solids level indicator assembly having mounting arms.
Figure 3:
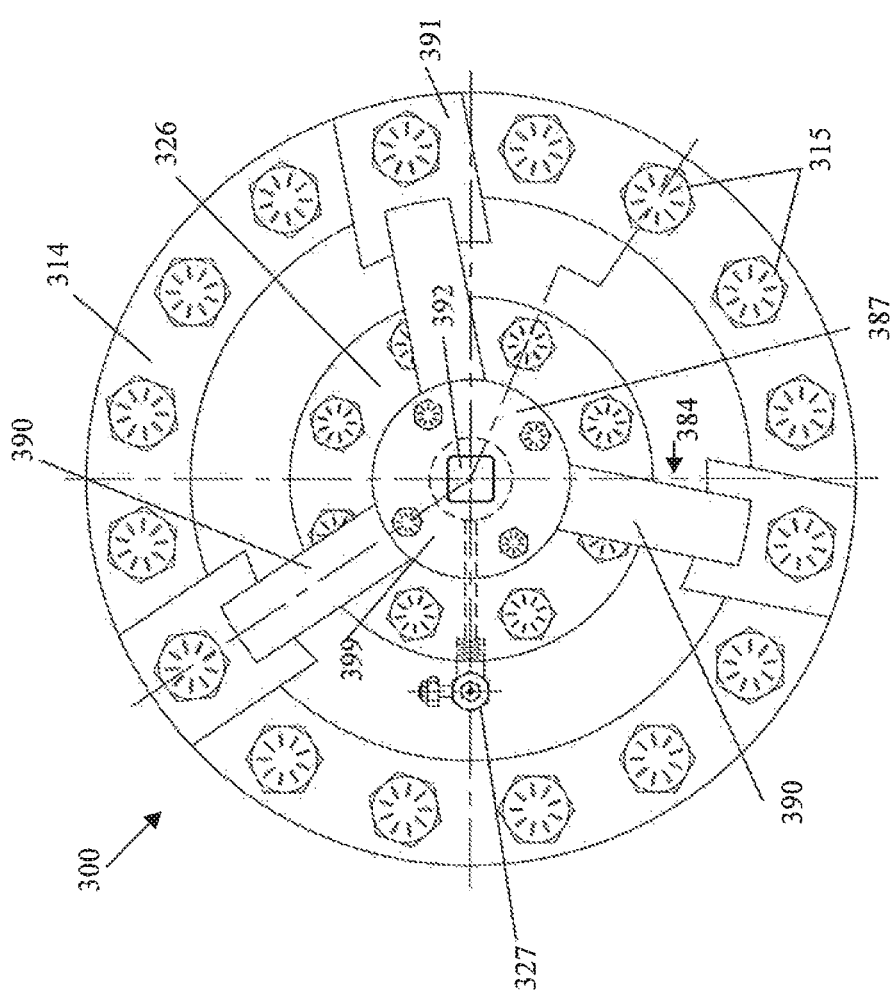
FIG. 3 illustrates an exemplary solids level indicator assembly having a modular external sensor, which is configured to be removed and is supported by mounting arms engaged to a vessel wall from a front view facing the vessel.
Figure 6:
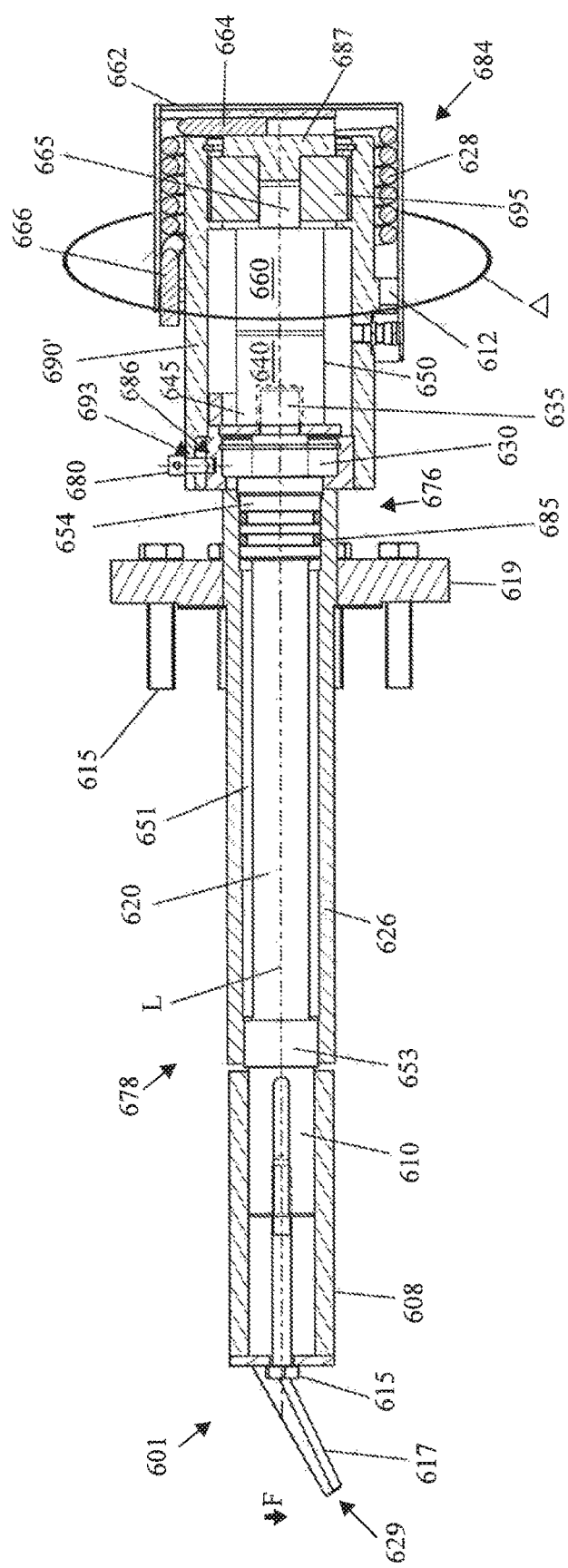
FIG. 6 illustrates a cross-sectional view of an exemplary solids level indicator where the support structure is a support sleeve and where the solids level indicator further comprises a torsion spring disposed around the support sleeve.

Although accompanying FIGS. 2 and 3 depict a support structure 284 and 384 respectively comprising three mounting arms 190, it will be understood that an exemplary support structure may comprise two or less mounting arms 190. Furthermore, other exemplary embodiments may have more than three mounting arms 190. In still further exemplary embodiments, a mounting cone may be used in lieu of the mounting arms 190. In FIG. 6, the support structure 684 comprises a support sleeve 690' engaged to the shaft housing exterior end 676 and a female adapter 675 adjacently disposed a male adapter 665 on the stationary end 660 of a modular external sensor 650. It will be understood that other support structures configured to vibrate with the solids level indicator 101 while the vessel 105 is active and thereby accommodate vibrations emanating from an active vessel 105, while further preventing the stationary end 160 of the modular external sensor 150 from rotating are within the scope of this disclosure. The shaft housing is one such example support structure.

The second end 199 of the mounting arms 190 may secure the stationary end 160 of the modular external sensor 150 and keep the stationary end 160 stationary by using a plug cap 195 disposed within the second end 199 of the mounting arms 190. In the depicted exemplary embodiment, the plug cap 195 does not engage the rotary end 140 of the modular external sensor 150 and thereby permits rotary movement. The plug cap 195 has a receptacle 175 adjacently disposed to the male adapter 165 extending from the stationary end 160 of the modular external sensor 150. A shear pin 180 extends through the second end 199 of the mounting arms 190 into the plug cap 195. Shear pins 180 may be used in areas where resistance to torsional or shear stress is weak. The shear pin 180 is configured to break with the shear stress resulting from the torsional force Δ exceeds a preconfigured threshold. That is, if the rotary end 140 rotates beyond capacity and begins to exert torsional force Δ on the stationary end 160 and by extension, the plug cap 195 above a preconfigured threshold, the shear pins 180 will generally break and allow the plug cap 195 and stationary end 160 to rotate until the torsional force Δ is neutralized. This is typically about 90 degrees from a horizontal line bisecting the torsion shaft (H in FIG. 8). The sleeve 124 further protects the paddle cap 108 and the paddle 117 from solids 102 when the paddle is in a neutral position, e.g. when the paddle 117 is oriented substantially parallel to the solids flow direction D. By allowing the external sensor 150 to rotate until the excess rotational force Δ is relieved, the paddle 117 the paddle typically rotates 90 degrees to the 6 o'clock position such that the paddle 117 is no longer in the direction of solids particle flow D. In this manner, a broken shear pin 180 permits damage to the paddle 117 to be avoided. The cover plate 187 holds the plug cap 195 in place and the plug cap 195 holds the modular external sensor 150 in place. In this manner, the plug cap 195 is in torsional communication with the stationary end 160 of the modular external sensor 150, but the shear pin 180 prevents the stationary end 160 from rotating when the shear stress is below a preconfigured threshold. If the torsion shaft 120, paddle 117, and modular external sensors 150 of an inactive solids level indicator remain intact, operators may re-set the solids level indicator 101 by returning the paddle 117 to a transverse position relative to the direction of solids flow D and by adding new shear pins 180. The torsion shaft 120 being adjacently disposed to the modular external sensor 150 may be referred to as a "torsion rod" in this disclosure and claims. The shear pin 180 is an example of a "shear lock" as claimed herein. It will be understood that a "shear lock" may be a shear pin, a magnet, a rare-earth magnet, torsion spring, or other locking mechanism designed to allow the torsion rod to rotate when the shear force exerted on the shear lock exceeds a predetermined shear force threshold.

In certain exemplary embodiments, a magnet disposed in the support structure facing an oppositely poled magnet in the torsion rod may be a desirable shear lock. When the solids bearing down on the paddle exceeds the magnetic force between the oppositely poled magnets, the torsion rod rotates to avoid further paddle damages. When the excess shear force subsides, operators can return the torsion rod to an active position, thereby allowing the oppositely poled magnets to re-engage without introducing a new shear pin 180. It will be understood that a shear lock may be used in a similar manner as the "shear pins" described herein.

In other exemplary embodiments, the plug cap 195 may be absent and the support structure (see 684, FIG. 6) may engage the stationary end 160 of the modular external sensor 150 directly so as to prevent rotary movement of the stationary end 160 of the modular external sensor 150 below a threshold of shear stress. In still other exemplary embodiments, the plug cap 195 may be absent and another modular external sensor may be adjacently disposed and in torsional communication with a first modular external sensor. In still further exemplary embodiments, an adapter may separate the first modular external sensor from the second adjacent modular external sensor. It will be understood that other types of end pieces that hold the stationary end 160 of the modular external sensor 150 in position can suffice, including using an overload spring type device (see FIG. 6) configured to release if too much force is applied. The support structure 184 may be held in place using the existing fasteners 115. In certain configurations, existing fasteners 115 may need to be extended to accommodate the support structure 184.

Fasteners 115 may secure a cover plate 187 to the second end 199 of the mounting arms 190. It will be understood that other structures configured to place an adjacently disposed plug cap 195 in torsional communication with the stationary end 160 of the modular external sensor 150 are considered to be within the scope of this disclosure. By way of example, these other structures may include a female adapter in the stationary end 160 and a male adapter on the plug cap 195. Other structures configured to place an adjacently plug cap 195 in torsional communication with stationary end 160 of the modular external sensor 150 may include, screws, bolts, pins, tacks, a combination of male and female adapters, adapters disposed between the modular external sensor 150 and the plug cap 195, magnets, or a combination thereof. In embodiments in which the plug cap 195 engages the stationary end 160, sealing mechanisms 185 such as O-rings, or mechanical seals may be placed between the second end 199 of the mounting arms 190 and the plug cap 195. In other embodiments, the sealing mechanisms 185 may be disposed between the mounting arms 190 and the stationary end 160 of the external sensor 150.

The modular external sensor 150 is configured to be slidably disengaged from the shaft exterior end 130. In instances in which the external sensor 150 becomes damaged, ceases to operate, or is desired to be removed, operators may unfasten the fasteners 115 that secure the external sensor 150 to the mounting arms 190. Operators may remove the cover plate 187 and extract the plug cap 195 before removing the modular external sensor 150 from the second end 199 of the mounting arms 190. Removing the external sensor 150 generally exposes the shaft exterior end 130. Because the modular external sensor is modular, operators may attach a replacement external sensor 150 to the shaft exterior end 130 before re-fastening the fasteners 115 to secure the external sensor 150 to the second end 199 of the mounting arms 190. The simple design of the modular external sensor 150 may allow operators to repair or replace a damaged external sensor 150 locally while the process is running, thereby eliminating delays caused by sending the modular external sensor 150 to third parties for repair.

An exemplary solids level indicator assembly 100 may be used with solids disposed within a vessel, but may be desirably used with lignocellulosic material such as wood chips, corn stover, bagasse, agricultural residue, grains, feed stock, and other such materials commonly used in the pulp and paper and biofuels industries.

FIG. 2 is a front view depicting three mounting arms 290 of the exemplary solids level indicator assembly 100. The first end 291 engages stabilizing structure (see 119, 113) connected to the vessel 105. Fasteners 215 may engage a plug cap 295 to the second end 299 of the mounting arms 290. In certain exemplary embodiments, a single mounting arm 290 may stabilize the stationary end 160 of the external sensor 150. In other exemplary embodiments, more than two mounting arms 290 may stabilize the stationary end 160 of the external sensor 150. In still other exemplary embodiments, a mounting cone may stabilize the external sensor 150. In embodiments utilizing a mounting cone, a means for accessing the modular external sensor are desirably included. This means may include a door, or area defining a hole in the cone.

FIG. 3 is a front view of an exemplary solids level indicator assembly 300 having three mounting arms 390 converging at the second end 399. Fasteners 315 engage the first end 391 of each mounting arm 390 to an adaptor flange 314 of the conduit 125. Fasteners may also engage the shaft housing 326 to the adaptor flange 314 of the conduit 125, or if the torsion shaft 120 has a smaller width or diameter than the conduit 125, fasteners 315 may alternatively engage the shaft housing 326 to an indicator adapter 113. Fasteners 315 may further engage a cover plate 387 to the second end 399 of the mounting arms 390. In this exemplary embodiment, the male adapter 365 of the stationary end 160 of the external sensor 150 can be seen through a hole in the center of the cover plate 387. Operators may lubricate the space between the torsion shaft 120 and the mounting arms 390 through the lubricant fitting 327.

Figure 4:
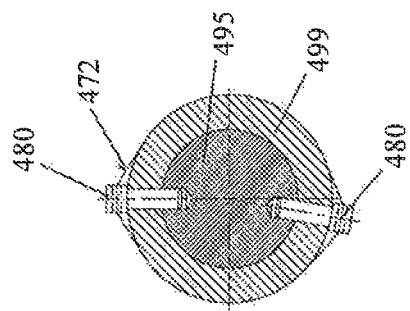
FIG. 4 shows shear pins extending through the second end of the mounting arms and into the cap plug in a front cross-sectional view.

FIG. 4 is a cross-sectional view of a plug cap 495 and the second end 499 of mounting arms 390. Shear pins 480 extend through the second end 499 mounting arms 390 and into the plug cap 495. A securing wire 472 extends through the heads of the shear pins 480 to secure the shear pins 480 to the second end 499 of the mounting arms 390. The shear pins 480 generally do not extend more than halfway between the center of the plug cap 495 and the outer surface of the plug cap 495. If the solid particles 102 impart too great a force F on the paddle 117, the paddle 117 transfers excessive torsional force Δ along the length L of the torsion shaft 120. The torsional force Δ turns the rotary end 140 of the modular external sensor 150, whereby the rotary end 140 may catch an edge within the stationary end 160 of the modular external sensor 150 and thereby becomes locked with the stationary end 160 of the modular external sensor 150. If the rotary end 140 continues to exert torsional force Δ on the stationary end 160 of the modular external sensor 150 beyond a desirable tolerance, the stationary end 160 also rotates, which in turn rotates the plug cap 495. The rotating plug cap 495 may break the shear pins 480, thereby relieving torsional force Δ and allowing the paddle 117 to become oriented substantially parallel relative to the direction of solid flow D. In certain exemplary embodiments, the shear pins 480 may be omitted. In other exemplary embodiments, the shear pins 480 may extend through a shaft housing 126 and into the torsion shaft 120.

Figure 5:
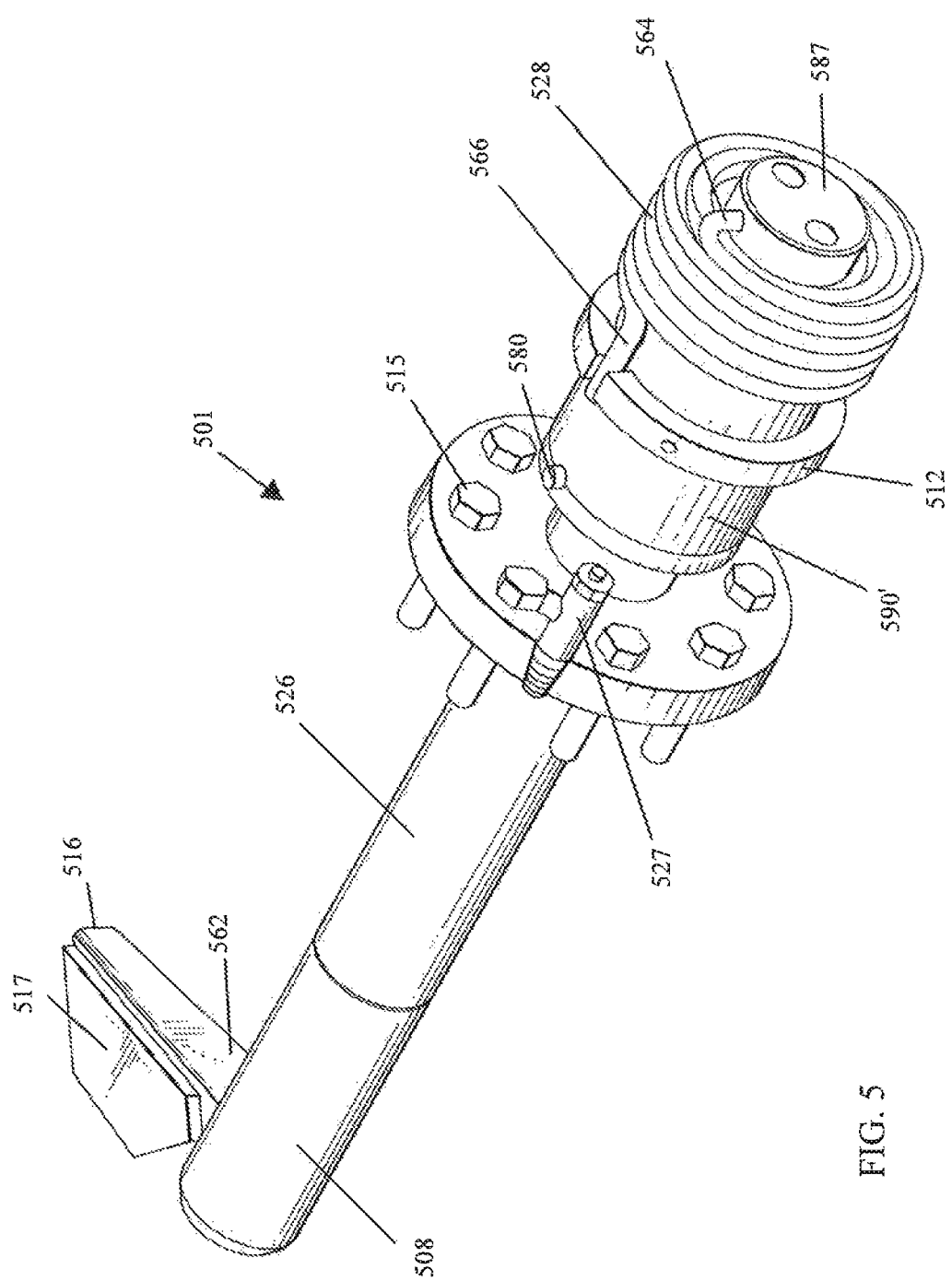
FIG. 5 is a perspective view of an exemplary solids level indicator assembly having a support sleeve in lieu of support arms and a torsion spring disposed around the support sleeve.

FIG. 5 is a perspective view of an exemplary solids level indicator 501 having a support sleeve 590' in lieu of one or more mounting arms 390. The support sleeve 590' may be machined from a single piece of material such as 2205 grade, 304L grade stainless steel, carbon steel, or other material configured to withstand vessel vibrations and the torsional force Δ the solids level indicator 501 may exhibit. A shear pin 580 engages the support sleeve 590' to the shaft housing 526. This view shows that a shear pin 580 may be added at a location configured to withstand a maximum torsional or shear force Δ such as at the junction between the shaft housing 526 and support sleeve 590'. A clamp 512 secures the second spring end 566 of the torsion spring 528 to the support sleeve 590'. The torsion spring 528 stores excess torsional force Δ transmitted through the torsion shaft 620 and shaft housing 526 to the support sleeve 590'.

FIG. 6 is a cross sectional view of an exemplary solids level indicator 601 having a support sleeve 690' in lieu of mounting arms 390. The shaft housing 626 encloses the torsion shaft 620. The shaft housing 626 extends into the vessel interior FIG. 1, 103. Fasteners 615 may secure the shaft housing 626 to the vessel 105. In certain embodiments, the fasteners 615 may secure the shaft housing 626 to the indicator adapter 113, which engages a mounting flange 119 extending through the vessel 105. Unlike the exemplary embodiment depicted in FIG. 1, a shear pin 680 extends through the support sleeve 690' into the shaft housing exterior end 676.

The rotary end 640 of the modular external sensor 650 engages the shaft exterior end 630. If the downward force F of the solid particles overcomes the resistance of the shaft housing 626, the torsion shaft 620 rotates, thereby rotating the rotary end 640 of the modular external sensor 650. In this manner, the torsion shaft 620 transmits torsional force Δ from the paddle 617 to the rotary end 640 of the modular external sensor 650. In certain exemplary embodiments, the modular external sensor 650 may be an angle gauge. In other exemplary embodiments, the angle gauge may be in torsional communication with the torsion shaft 620, but the angle gauge is disposed outside of the support structure 684. In still further exemplary embodiments, another modular external sensor (not depicted) may be in torsional communication with the torsion shaft 620 but disposed outside of the support structure 684. The angle gauge may calculate the torsion and chip level based on the change in angle from a neutral reference point. When the downward force F on the paddle 617 becomes too great, the rotary end 640 and the stationary end 660 of the modular external sensor 650 lock, thereby placing the stationary end 660 in torsional communication with the torsion shaft 620. In the depicted embodiment, the male adapter 665 extending from the stationary end 660 of the modular external sensor 650 transmits the torsional force Δ to a cover plate 687 through a plug cap 695. The cover plate 687 engages a spring first end 664 of a torsion spring 628 oppositely disposed from a second spring end 666 of the torsion spring 628. The torsion spring 628 encircles the support sleeve 690'. A clamp 612 disposed around the outer diameter of the support sleeve 690' tightly engages the second spring end 666 to the support sleeve 690'

As the paddle 617 rotates in response to downward force F, the modular external sensor 650 measures the change in torsion by calculating the rotation of the rotary end 640 relative to the stationary end 660. When the downward force F and torsional force Δ exceed the modular external sensor's capacity, the rotary end 640 locks with the stationary end 660 thereby placing the rotary end 640, stationary end 660, plug cap 695, cover plate 687, and torsion spring 628 in torsional communication with the torsion shaft 620. The torsion spring 628 stores the excess torsional force Δ transmitted through the torsion shaft 620 and thereby prevents frequent wear and loosening of the support sleeve 690' relative to the shaft housing 626.

Furthermore, when the excess torsional force Δ subsides, the torsion spring 628 transmits its stored potential energy back through the cover plate 687, plug cap 695, modular external sensor 650, torsion shaft 620 and ultimately the paddle 617 to counter the downward force F of the solids 102 in the vessel 105. In this manner, the paddle 617 can return automatically to a position that crosses the downward flow D of the solid particles 102 after excessive forces have subsided. In this manner, the exemplary embodiment thereby protects the paddle 617 when the downward force F is excessive and allowing the paddle 617 and the solids level indicator 601 to continue to measure the solids level when the excessive force has subsided.

Similarly, if the torsional force Δ exceeds the torsion spring's 628 capacity, the second spring end 666 and clamp 612 transmits the excess stored torsional force Δ through the support sleeve 690' to shear pin 680 extending through a shear pin hole 693 in the support sleeve 690' and a shaft housing bore hole 686. By extending through shear pin hold 693 and shaft housing bore hole 680, the shear pin 680 experiences the excess stored torsional force Δ as shear force. The shear pin generally has a thickness and is made of material configured to withstand torsional force Δ below a predetermined threshold. If the excess stored torsional force transmitted through the support sleeve 690' exceeds the maximum torsional force the shear pin 680 was configured to withstand, the shear pin 680 will break and the paddle 617 will rotate to a neutral, vertical position. The neutral vertical position protects the paddle 617 against the overbearing mass of the solid particles 102, but further prevents the modular external sensor 650 from measuring the solids level. However, if the torsion spring 628 is not deformed or rendered non-functional by the excessive force, the torsion spring will return the paddle 617 at least partially to a transverse position relative to the flow direction of the solid particles D, thereby allowing the solids level indicator 601 to retain functionality without shear pins 680. In exemplary embodiments, the shear pin 680 may connect the support sleeve 690' to the shaft housing 626. In other exemplary embodiments, the shear pin 680 may connect the support sleeve 690' to the torsion shaft 620, or other element at a point less equipped to withstand torsional force Δ.

In further exemplary embodiments, the torsion spring 628 may be pre-loaded with torque to align the torsion spring 628 with the outer surface of the support structure 684. In still other exemplary embodiments, the shear pin 680 may be omitted in embodiments comprising a torsion spring 628, wherein the torsion spring 628 is configured to store torsional force Δ sufficient to allow the paddle to rotate 90° downwardly from a horizontal line (H in FIG. 8) bisecting the torsion shaft 620.

When a person desires to replace the modular external sensor 650, the person may disengage the first spring end 664 from the cover plate 687 and remove the cover plate 687 from the solids level indicator 601. The person may further remove the plug cap 695 to expose the stationary end 660 of the modular external sensor 650. A person may then extract the modular external sensor 650 from the solids level indicator 601 without being exposed to the process conditions within the vessel 105. The person may then insert a new modular external sensor 650 through the support sleeve 690' until the receptacle 645 on the rotary end 640 of the modular external sensor 650 is adjacently disposed to the male adaptor 635 on the shaft exterior end 630. In the manner, the person can place a new modular external sensor 650 in torsional communication with the torsion shaft 620 without removing the torsion shaft 620 or paddle 617 from the vessel 105, thereby preventing the person from being exposed to vessel process conditions while the vessel is operational.

Figure 7:
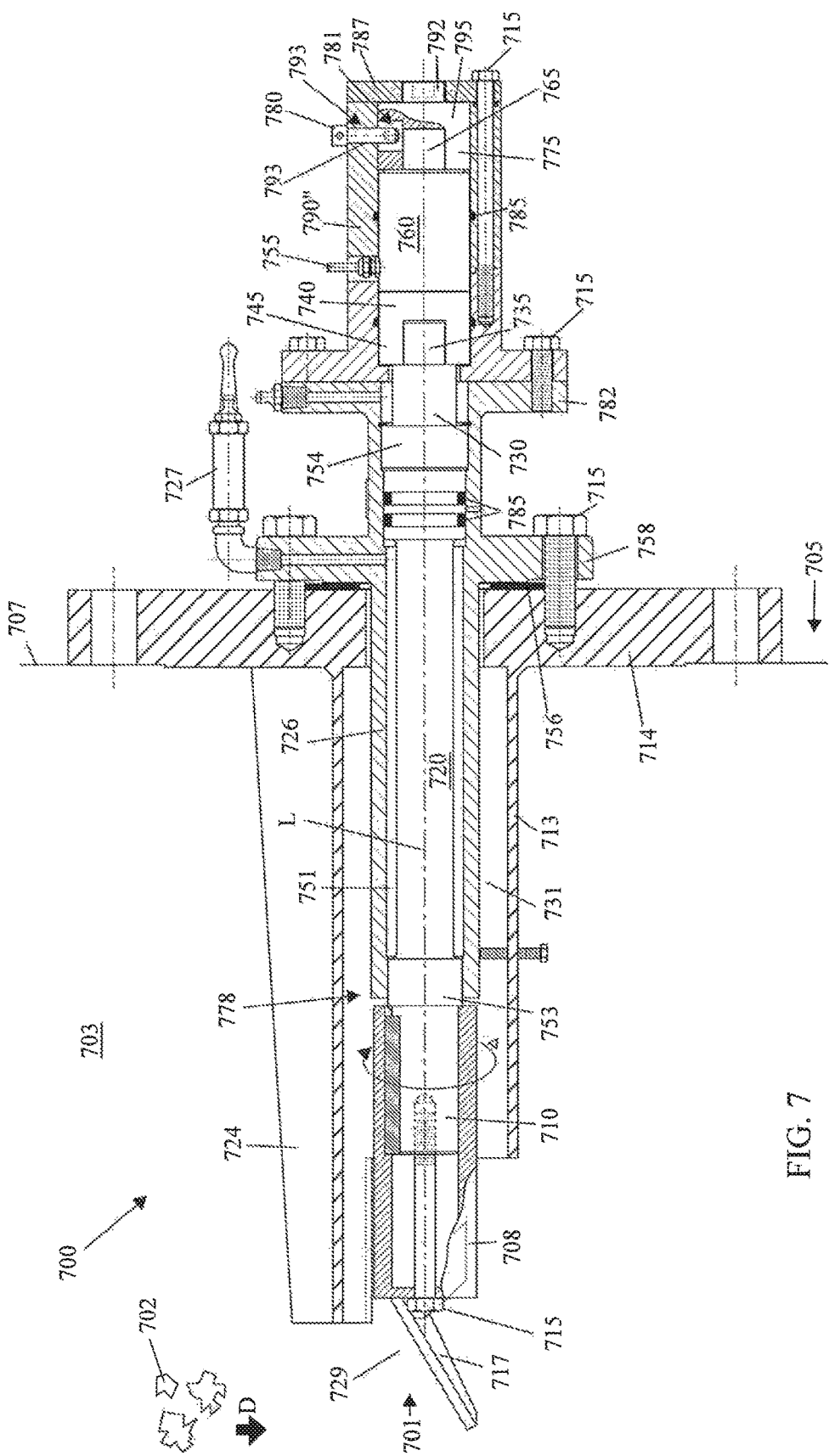
FIG. 7 depicts an exemplary solids level indicator assembly having a support sleeve for a support structure wherein the solids level indicator has a multi-bore plug cap in a cross-sectional view.

FIG. 7 is a cross-sectional view of an exemplary solids level indicator assembly 700 where a support sleeve 790" engaged to the shaft housing 726 comprises the support structure 784. Fasteners 715 engage a first flange 758 of the shaft housing 726 to the indicator adaptor 713. A gasket 756 may be disposed between the first flange 758 and the indicator adaptor 713 or indicator adaptor flange 714. The shaft exterior end 730 extends through a second flange 757 on the housing exterior end 776. The second flange 757 is oppositely disposed from the first flange 758. The shaft exterior end 730 comprises a male adapter 735. The receptacle 745 on the rotary end 740 of the modular external sensor 750 tightly encloses the male adaptor 735 and thereby is in torsional communication with the adjacently disposed torsion shaft 720. Similarly, the cap plug's receptacle 775 tightly encloses a male adaptor 765 extending from the stationary end 760 of the modular external sensor 750. Fasteners 715 engage a support sleeve flange 782 to the second flange 757 of shaft housing 726. One or more shear pins 780 extend through an area defining a shear pin hole 793 in the support sleeve 790" into areas in the plug cap 795 defining a bore hole 781 thereby rendering immobile the plug cap 780 and the adjacently disposed stationary end 760 of the modular external sensor 750. If a person desires to replace the modular external sensor 750, the person may remove the fasteners 715 that engage the support sleeve 790" to the shaft housing 726 and subsequently remove the support sleeve 790" to expose the modular external sensor 750 in other exemplary methods, a person may remove the cover plate 787, remove the shear pin 780, and remove the plug cap 795 before accessing the modular external sensor 750. The modular external sensor 750 may be removed from the support sleeve 790".

FIG. 8 is a front view of an exemplary solids level indicator assembly 800 depicting horizontal line H bisecting torsion shaft 720 (see 892). Indicator adaptor 813 extends into the vessel wall 807. A lubricant fitting 827 allows operators to introduce grease or other lubricant or coolant into grease channel 751.

Figure 9A:
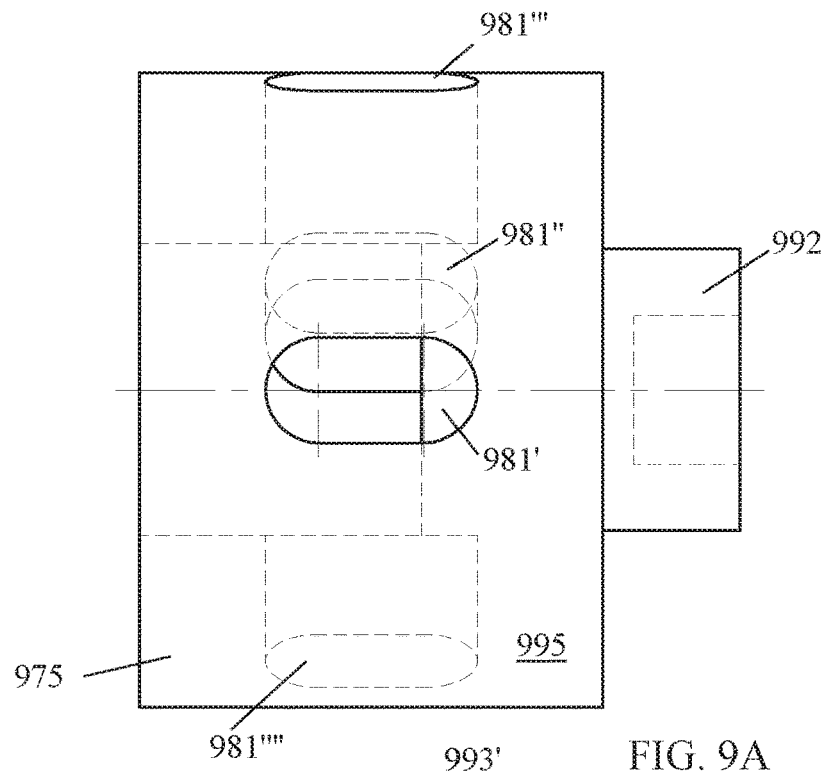
FIG. 9A depicts a side view of an exemplary multi-bore plug cap as used in the embodiments shown in FIGS. 7 and 8.
Figure 9B:
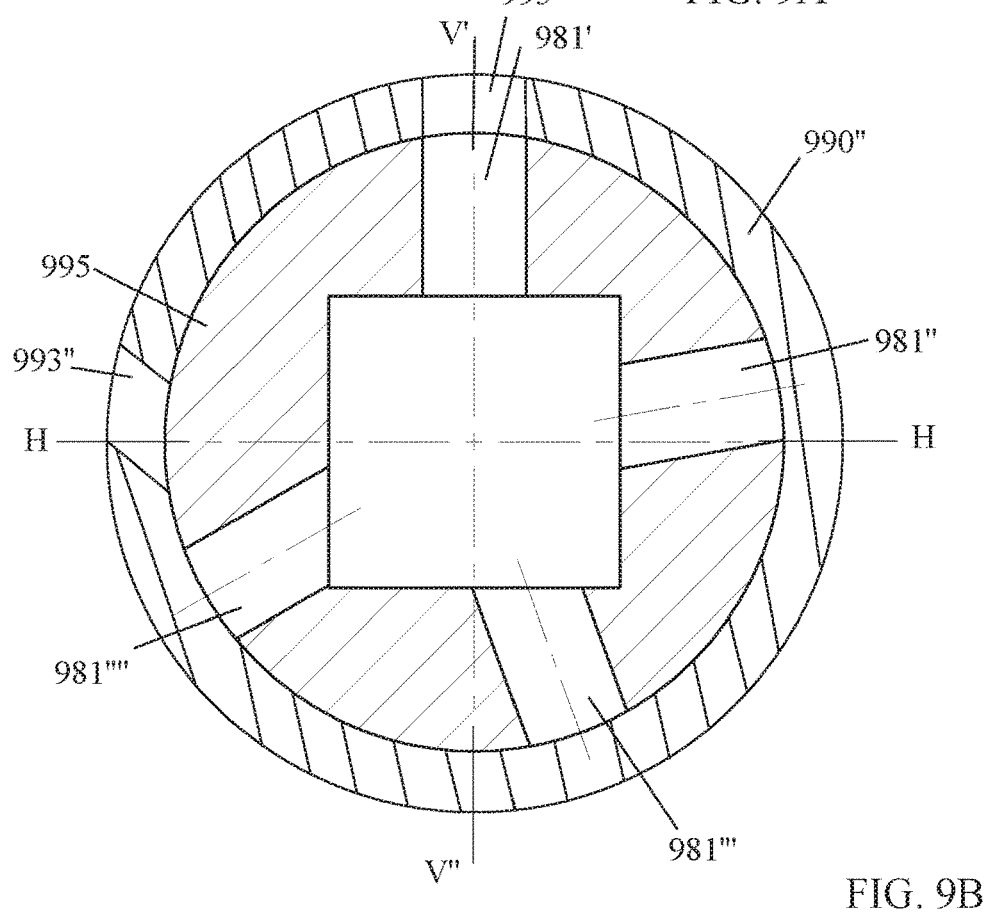
FIG. 9B is a cross-sectional front view of an exemplary multi-bore cap as shown in FIGS. 7 and 8.

FIG. 9A depicts an exemplary plug cap 995 comprising multiple bore holes 981 extending radially into the plug cap 995 at intervals. In certain exemplary embodiments, the intervals may be regular intervals. In other exemplary embodiments, the intervals may be irregular intervals. For example, FIG. 9B shows a first bore hole 981' at a twelve o'clock position. In the embodiment depicted in FIG. 7, the paddle 717 is at an angle of 0 degrees (°) relative to a horizontal line (H in FIG. 8) bisecting the torsion shaft 720 when the shear pin 780 extends through the shear pin hole 793 and into the first bore hole 981'. A second bore hole 981" may be disposed a number of degrees from the first bore hole 981'. For example, the second bore hole 981" may be disposed 10° from the first bore hole 981'. A third bore hole 981'" may be disposed a number of degrees from the second bore hole 981". In further exemplary embodiments, a fourth bore hole 981"" may be deposed a number of degrees from the third bore hole 981'". In still further exemplary embodiments, a fifth and subsequent bore holes may be disposed at intervals after each preceding bore hole.

FIG. 9B further depicts a support sleeve 990" having a shear pin hole 993' disposed at the twelve o'clock position, which is zero degrees from the vertical reference line V'. A second shear pin hole 993" is disposed in the support sleeve 990". For example the second shear pin hole 993" may be disposed 85 degrees from the vertical reference line V'.

Operators may angle the paddle 717 under the horizontal line H to reduce effectively the surface area exposed to the downwardly flowing solid particles 702. For example, if the third bore hole 981'" is disposed 30° from the first bore hole 981, an operator may turn the plug cap 995 30° from the first bore hole 981' to align the third bore hole 981'" with the first shear pin hole 993' in the support sleeve 990". The plug cap 995, being in torsional communication with the modular external sensor 750 and the torsion shaft 720, turns the torsion shaft 720 and paddle 717 below the horizontal line H by 30°. Without being bounded by theory, this angle may deflect some force of the downwardly flowing solid particles 702 and thereby discard a portion of the downward force F that the paddle 717 engaged to the shaft interior end 710 would otherwise convert into torsional force Δ. The degree of deflection below the horizontal line H may vary depending upon the height at which the solids level indicator 701 is disposed within the vessel 705. For example, in vapor phase chemical digesters, a solids level indicator 701 located in an upper zone of the digester may have an angle of paddle deflection that is greater than the angle of paddle deflection in a solids level indicator 701 701 disposed under the liquor. The multiple bore holes 981 further allow operators to adjust the angle of the paddle 717 while the vessel 705 remains operational. In this manner, operators may reduce or increase each solids level indicator 701 receives at each location along the height of the digester wall 707 to respond to fluctuating operating conditions.

In the depicted embodiment, the second shear pin hole 993" allows operators to set the paddle deflection angle at intervals between the intervals defined by the first shear pin hole 993'. By way of example, the angle of the paddle 717 relative to the vertical reference line V'" may be 90 degrees when a shear pin 780 extends through first bore hole 981' and first shear pin hole 993'. Relative the vertical reference line V'", the paddle deflection angle may be 80 degrees when the shear pin 780 extends through first shear pin hole 993' and second bore hole 981", 70 degrees at first shear pin hole 993' and third bore hole 981'" first shear pin hole 993' and second bore hole 981'", and 60 degrees at first shear pin hole 993' and fourth bore hole 981"". Similarly by way of example, the paddle deflection angle may be 85 degrees relative to vertical reference line V" when a shear pin 780 extends through second shear pin hole 993" and first bore hole 981', 75 degrees at second shear pin hole 993" and second bore hole 981", 65 degrees at second shear pin hole 993" and third bore hole 981'", and 55 degrees at second shear pin hole 993" and fourth bore hole 981"". The second shear pin hole 993" is desirably disposed at a position less than 90 degrees from the first shear pin hole 993' relative to vertical reference line V'.

It will be understood that the first bore hole 981' need not be located at the 12 o'clock position. Other arrangement of bore holes 981 shear pins 780, and other shear locks, that permit an operator to adjust the angle of the paddle 717 relative to a horizontal line H bisecting the torsion shaft 720 is considered to be within the scope of this disclosure.

An exemplary solids level indicator assembly comprises: a shaft housing having a housing interior end oppositely disposed a housing exterior end, wherein the shaft housing exterior end is disposed outside a vessel, and wherein the shaft housing fixedly engages the vessel so as to resist torsional movement, a solid torsion shaft having a shaft interior end and a shaft exterior end, wherein the solid torsion shaft is disposed within the shaft housing such that the shaft interior end extends past the housing interior end to engage a paddle cap disposed within the vessel, a paddle engaging the paddle cap perpendicularly to a length of the solid torsion shaft so as to cross a path of solid particles in the vessel, wherein the paddle torsionally communicates with the shaft interior end, a modular external sensor having a rotary end adjacently disposed to a stationary end, wherein the rotary end is adjacently disposed to the shaft exterior end and the shaft exterior end torsionally communicates with the adjacently disposed rotary end, and wherein the modular external sensor is configured to be slidably disengaged from the shaft exterior end, wherein the modular external sensor being adjacently disposed to the shaft exterior end defines a torsion rod, a support structure engaged to the solids level indicator assembly, and a shear lock configured to engage the support structure to the torsion rod, wherein the shear structure is configured to withstand a maximum shear force and wherein the support structure and the shear structure are configured to prevent the torsion rod from rotating when the shear force does not exceed the maximum shear force.

In the exemplary solids level indicator assemblies the vessel may be selected from the group consisting of a vapor phase chemical digester, a hydraulic phase chemical digester, and an impregnation vessel.

In a further exemplary embodiment, a solids level indicator comprises: a shaft housing having a housing interior end and a housing exterior end, wherein the shaft housing exterior end is disposed outside a vessel, and wherein the shaft housing fixedly engages the vessel so as to resist torsional movement, a solid torsion shaft having a shaft interior end and a shaft exterior end, wherein the solid torsion shaft is disposed within the shaft housing such that the shaft interior end extends past the housing interior end to engage a paddle cap disposed within the vessel, a paddle engaging the paddle cap perpendicularly to a length of the solid torsion shaft so as to cross a path of solid particles in the vessel, wherein the paddle torsionally communicates with the shaft interior end, a modular external sensor having a rotary end adjacently disposed to a stationary end, wherein the rotary end is adjacently disposed to the shaft exterior end and the shaft exterior end torsionally communicates with the adjacently disposed rotary end, and wherein the modular external sensor is configured to be slidably disengaged from the shaft exterior end, a support structure engaged to the solids level indicator assembly, and a torsion spring disposed around the support structure, wherein the torsion spring has a first spring end distally disposed from a second spring end, wherein the first spring end is in torsional communication with the modular external sensor, and wherein second spring end fixedly engages the support structure such that the torsion spring bends to store torsional energy when solids exert a downward force on the paddle and wherein the torsion spring releases the stored energy into the solid torsion shaft in a direction opposite the direction of the torsional force exerted on the paddle by the mass of solids when the force exerted by the solids subsides.

In a further exemplary embodiment, the solids level indicator comprises: a shaft housing having a housing interior end and a housing exterior end, wherein the shaft housing exterior end is disposed outside a vessel, and wherein the shaft housing fixedly engages the vessel so as to resist torsional movement, a solid torsion shaft having a shaft interior end and a shaft exterior end, wherein the solid torsion shaft is disposed within the shaft housing such that the shaft interior end extends past the housing interior end to engage a paddle cap disposed within the vessel, a paddle engaging the paddle cap perpendicularly to a length of the solid torsion shaft so as to cross a path of solid particles in the vessel, wherein the paddle torsionally communicates with the shaft interior end, a modular external sensor having a rotary end adjacently disposed to a stationary end, wherein the rotary end is adjacently disposed to the shaft exterior end and the shaft exterior end torsionally communicates with the adjacently disposed rotary end, and wherein the modular external sensor is configured to be slidably disengaged from the shaft exterior end, a support structure engaged to the solids level indicator assembly, wherein the support structure has an area defining a shear pin hole, a shear pin, and a multi-bore plug cap, wherein the plug cap torsionally communicates with the stationary end of the modular external sensor, wherein the plug cap has areas defining bore holes extending radially into the plug cap at intervals, such that a bore hole of the multiple bore holes aligns with the shear pin hole in the support structure, and wherein the shear pin extends through the shear pin hole into the bore hole define a paddle deflection angle with respect to a horizontal line bisecting the solid torsion shaft, wherein the shear pin is configured to withstand a maximum shear force, and wherein the shear pin and support structure are configured to prevent the stationary end of the modular external sensor from rotating when the shear force does not exceed the maximum shear force.

The exemplary assemblies may further comprise multiple modular external sensors in torsional communication with the torsion shaft wherein each modular external sensor is configured to be slidably removed from the solids level indicator assembly.

A solids level indicator assembly has been conceived comprising a shaft having an interior end and an exterior end, wherein the interior end may be disposed within a vessel, wherein the shaft can be configured to fixedly engage a housing so as to resist torsional force. The assembly may desirably have a paddle transversely disposed on the interior end of the shaft so as to cross the path of solid particles in the vessel, an external sensor configured to be detached from the exterior end of the shaft, the external sensor comprising a rotary end and a stationary end, and a support structure engaged to the solids level indicator assembly, wherein the support structure can be configured to prevent the stationary end of the external sensor from rotating within a predetermined range of torsional force.

The shaft may be disposed within a conduit defining an opening between a vessel interior and a vessel exterior. The support structure may be mounting arms having a first end engaging the conduit and a second end configured to engage the stationary end of an external sensor. In certain exemplary embodiments, an adapter may be disposed between the conduit and the first end of the mounting arms. In other exemplary embodiments, the support structure may be a mounting cone.

In still other exemplary embodiments, the support structure may be a support sleeve having a first end and a second end, wherein the first end engages the housing. The support sleeve may further have a torsion spring in which the first end of the torsion spring engages a cover plate and the second end of the torsion spring engages the support sleeve so as to store torsional force transmitted through the shaft.

While this invention has been particularly shown and described with references to exemplary embodiments thereof, it will be understood by those skilled in the art that various changes in form and details may be made therein without departing from the scope of the invention encompassed by the appended claims.

What is claimed is:

1. A solids level indicator assembly comprising:
    a shaft housing having a housing interior end oppositely disposed a housing exterior end, wherein the shaft housing exterior end is disposed outside a vessel, and wherein the shaft housing fixedly engages the vessel so as to resist torsional movement;
    a torsion shaft having a shaft interior end and a shaft exterior end, wherein the torsion shaft is disposed within the shaft housing such that the shaft interior end extends past the housing interior end to engage a paddle cap disposed within the vessel;
    a paddle engaging the paddle cap perpendicularly to a length of the torsion shaft so as to cross a path of solids in the vessel, wherein the paddle torsionally communicates with the shaft interior end;
    a modular external sensor having a rotary end adjacently disposed to a stationary end, wherein the rotary end is adjacently disposed to the shaft exterior end and the shaft exterior end torsionally communicates with the adjacently disposed rotary end, and wherein the modular external sensor is configured to be disengaged from the shaft exterior end, wherein the modular external sensor being adjacently disposed to the shaft exterior end defines a torsion rod;
    a support structure engaged to the solids level indicator assembly, and;
    a shear lock configured to engage the support structure to the torsion rod, wherein the shear lock is configured to withstand a maximum shear force and wherein the support structure and the shear lock are configured to prevent the torsion rod from rotating when the shear force does not exceed the maximum shear force.

2. The assembly of claim 1, wherein the support structure is selected from the group consisting of mounting arms, a mounting cone, and a support sleeve, shaft housing, or a combination thereof.

3. The assembly of claim 1 further comprising an indicator adaptor having a protective sleeve extending over the paddle cap, wherein the indicator adaptor is configured to fixedly engage a solids level indicator to a vessel wall so as to resist torsional movement.

4. The assembly of claim 1 further comprising a plug cap adjacently disposed to the stationary end of the modular external sensor wherein the plug cap torsionally communicates with the stationary end of the modular external sensor, wherein the plug cap has areas defining a bore hole, and wherein the shear lock is a shear pin extending through a shear pin hole in the support structure into the bore hole of the plug cap to prevent the plug cap from rotating as long as the shear force does not exceed the maximum shear force.

5. The assembly of claim 4, wherein the plug cap has multiple bore holes arranged at intervals.

6. The assembly of claim 1 further comprising a torsion spring having a first spring end and a second spring end, wherein the first spring end engages a cover plate and is in torsional communication with the torsion shaft and the second spring end engages the support sleeve so as to store torsional force transmitted through the torsion shaft.

7. The assembly of claim 6, wherein the shear lock is a shear pin extending into the shaft housing and wherein the second spring end is configured to convey excess stored torsional force through the support structure to the shear pin.

8. The assembly of claim 1, wherein the modular external sensor is selected from the group consisting of a strain gauge, a piezoelectric sensor, an angle gauge, torque transducer, or a combination thereof.

9. The assembly of claim 1 further comprising multiple modular external sensors in torsional communication with the torsion shaft and wherein each modular external sensor is configured to be slidably removed from the solids level indicator assembly.

10. The assembly of claim 1, wherein the vessel is selected from the group consisting of a vapor phase chemical digester, a hydraulic phase chemical digester, and an impregnation vessel.

11. The assembly of claim 1, wherein the shear lock is selected form the group consisting of a shear pin, a magnet, a rare earth magnet, torsion spring, or other structure configured to permit the torsion rod to rotate once the shear force exceeds a preconfigured shear force threshold.

12. A solids level indicator comprising:
 a shaft housing having a housing interior end and a housing exterior end, wherein the shaft housing exterior end is disposed outside a vessel, and wherein the shaft housing fixedly engages the vessel so as to resist torsional movement;
 a torsion shaft having a shaft interior end and a shaft exterior end, wherein the torsion shaft is disposed within the shaft housing such that the shaft interior end extends past the housing interior end to engage a paddle cap disposed within the vessel;
 a paddle engaging the paddle cap perpendicularly to a length of the torsion shaft so as to cross a path of solids in the vessel, wherein the paddle torsionally communicates with the shaft interior end;
 a modular external sensor having a rotary end adjacently disposed to a stationary end, wherein the rotary end is adjacently disposed to the shaft exterior end and the shaft exterior end torsionally communicates with the adjacently disposed rotary end, and wherein the modular external sensor is configured to be slidably disengaged from the shaft exterior end;
 a support structure engaged to the solids level indicator assembly; and
 a torsion spring disposed around the support structure, wherein the torsion spring has a first spring end distally disposed from a second spring end, wherein the first spring end is in torsional communication with the modular external sensor, and wherein second spring end fixedly engages the support structure such that the torsion spring bends to store torsional energy when solids exert a downward force on the paddle and wherein the torsion spring releases the stored energy into the torsion shaft in a direction opposite the direction of the torsional force exerted on the paddle by the mass of solids when the force exerted by the solids subsides.

13. The solids level indicator of claim 12 further comprising a shear pin extending through the support structure into the shaft housing.

14. The solids level indicator of claim 12, wherein the support structure is selected from the group consisting of mounting arms, a mounting cone, shaft housing, and a support sleeve, or a combination thereof.

15. The solids level indicator of claim 12, wherein the modular external sensor is selected from the group consisting of a strain gauge, a piezoelectric sensor, an angle gauge, torque transducer, or a combination thereof.

16. The solids level indicator of claim 12 further comprising multiple modular external sensors in torsional communication with the torsion shaft wherein each modular external sensor is configured to be slidably removed from the solids level indicator assembly.

17. A solids level indicator comprising:
 a shaft housing having a housing interior end and a housing exterior end, wherein the shaft housing exterior end is disposed outside a vessel, and wherein the shaft housing fixedly engages the vessel so as to resist torsional movement;
 a torsion shaft having a shaft interior end and a shaft exterior end, wherein the torsion shaft is disposed within the shaft housing such that the shaft interior end extends past the housing interior end to engage a paddle cap disposed within the vessel;
 a paddle engaging the paddle cap perpendicularly to a length of the torsion shaft so as to cross a path of solids in the vessel, wherein the paddle torsionally communicates with the shaft interior end;
 a modular external sensor having a rotary end adjacently disposed to a stationary end, wherein the rotary end is adjacently disposed to the shaft exterior end and the shaft exterior end torsionally communicates with the adjacently disposed rotary end, and wherein the modular external sensor is configured to be slidably disengaged from the shaft exterior end;
 a support structure engaged to the solids level indicator assembly, wherein the support structure has an area defining a shear pin hole;
 a shear pin; and
 a multi-bore plug cap, wherein the plug cap torsionally communicates with the stationary end of the modular external sensor, wherein the plug cap has areas defining bore holes extending radially into the plug cap at intervals, such that a bore hole of the multiple bore holes aligns with the shear pin hole in the support structure, wherein the shear pin extends through the shear pin hole into the bore hole to orient the plug cap, wherein the orientation of the plug cap defines a paddle deflection angle with respect to a horizontal line bisecting the torsion shaft, wherein the shear pin is configured to withstand a maximum shear force, and wherein the shear pin and support structure are configured to prevent the stationary end of the modular external sensor from rotating when the shear force does not exceed the maximum shear force.

18. The solids level indicator of claim 17, wherein the bore holes extend radially into the plug cap at regular intervals.

19. The solids level indicator of claim 17, wherein the bore holes extend radially into the plug cap at irregular intervals.

20. The solids level indicator of claim 17, wherein the multi-bore plug cap has four bore holes.

21. The solids level indicator of claim 17, wherein the multi-bore plug cap has eight bore holes and wherein the support structure has a second shear pin hole angularly offset from a first shear pin hole by less than 90 degrees.

22. The solids level indicator of claim 17, wherein the support structure is selected from the group consisting of mounting arms, a mounting cone, shaft housing, and a support sleeve, or a combination thereof.

23. The solids level indicator of claim 17, wherein the modular external sensor is selected from the group consisting of a strain gauge, a piezoelectric sensor, an angle gauge, torque transducer, or a combination thereof.

24. The solids level indicator of claim 17 further comprising multiple modular external sensors in torsional communication with the torsion shaft wherein each modular external sensor is configured to be slidably removed from the solids level indicator assembly.

* * * * *